United States Patent [19]

Chuan-Chih

[11] Patent Number: 4,747,408

[45] Date of Patent: May 31, 1988

[54] PORTABLE SAUNA-BATH JACKET

[76] Inventor: Huang Chuan-Chih, P.O. Box 10160, Taipei, Taiwan

[21] Appl. No.: 88,648

[22] Filed: Aug. 24, 1987

[51] Int. Cl.[4] ........ A61F 7/00

[52] U.S. Cl. ........ 128/400; 128/402; 128/379

[58] Field of Search ........ 128/400, 402, 403, 379

[56] References Cited

U.S. PATENT DOCUMENTS

| | | | |
|---|---|---|---|
| 2,255,751 | 9/1941 | Bancel | 128/402 |
| 2,832,336 | 4/1958 | Davis et al. | 128/402 |
| 3,125,865 | 3/1964 | Bemelman | 128/400 |
| 3,307,554 | 3/1967 | Thornton et al. | 128/400 |
| 3,507,321 | 4/1970 | Palma | 128/400 |
| 3,610,251 | 10/1971 | Sanderson | 128/400 |
| 3,738,367 | 6/1973 | Hardy | 128/400 |
| 3,918,458 | 11/1975 | Mathery | 128/400 |
| 4,149,529 | 4/1979 | Copeland et al. | 128/400 |

*Primary Examiner*—Ira S. Lazarus
*Assistant Examiner*—Sue Hagarman

[57] ABSTRACT

A portable sauna-bath jacket includes a one-piece jacket, a hot-air supplier, a cooling-water supplier, and a sequential timing device alternatively controlling the delivery of either a hot air or cooling water stream into the jacket for alternatively warming or cooling a bather for taking a sauna bath directly in the jacket for convenient, economic and hygienic purposes.

2 Claims, 3 Drawing Sheets

PORTABLE SAUNA-BATH JACKET

BACKGROUND OF THE INVENTION

When taking a conventional sauna both, a fixed box is provided to deliver hot air therein for warming a bather, thereby expanding his or her blood vessels. Then, the bather will leave the hot-air box and suddenly take a shower by spraying cooling water on his or her body to contract the blood vessels. By performing the hot-air bath and cooling-water bath alternatively, the bather will be comfortable since the alternative expansion and contraction of his or her blood vessels may enforce the blood circulation and relax the nervous system to soothe the tiredness especially after doing a heavy work.

However, such a fixed box for hot air and the cooling-water shower are separatedly installed in a bathe room. For taking such a bath, the bather should come to a paid public bath room to possibly waste time and cost or to be infected with diseases, unless he or she personally has installed such an equipment at his or her home. Still, the bather should always change the bathing equipments to cause inconvenience or tiredness due to his or her to-and-from moving between the hot-air box and the cooling-water shower.

Therefore, the present inventor invents the present portable sauna-bath jacket.

SUMMARY OF THE INVENTION

The object of the present invention is to provide a portable sauna-bath jacket including an one-piece jacket, a hot-air supplier, a cooling-water supplier and a sequential timing device alternatively controlling the delivery of either a hot air or cooling water stream into the jacket for alternatively warming or cooling a bather for taking a sauna bath directly in the jacket for convenient, economic and hygienic purposes.

DETAILED DESCRIPTION

Figure 1:
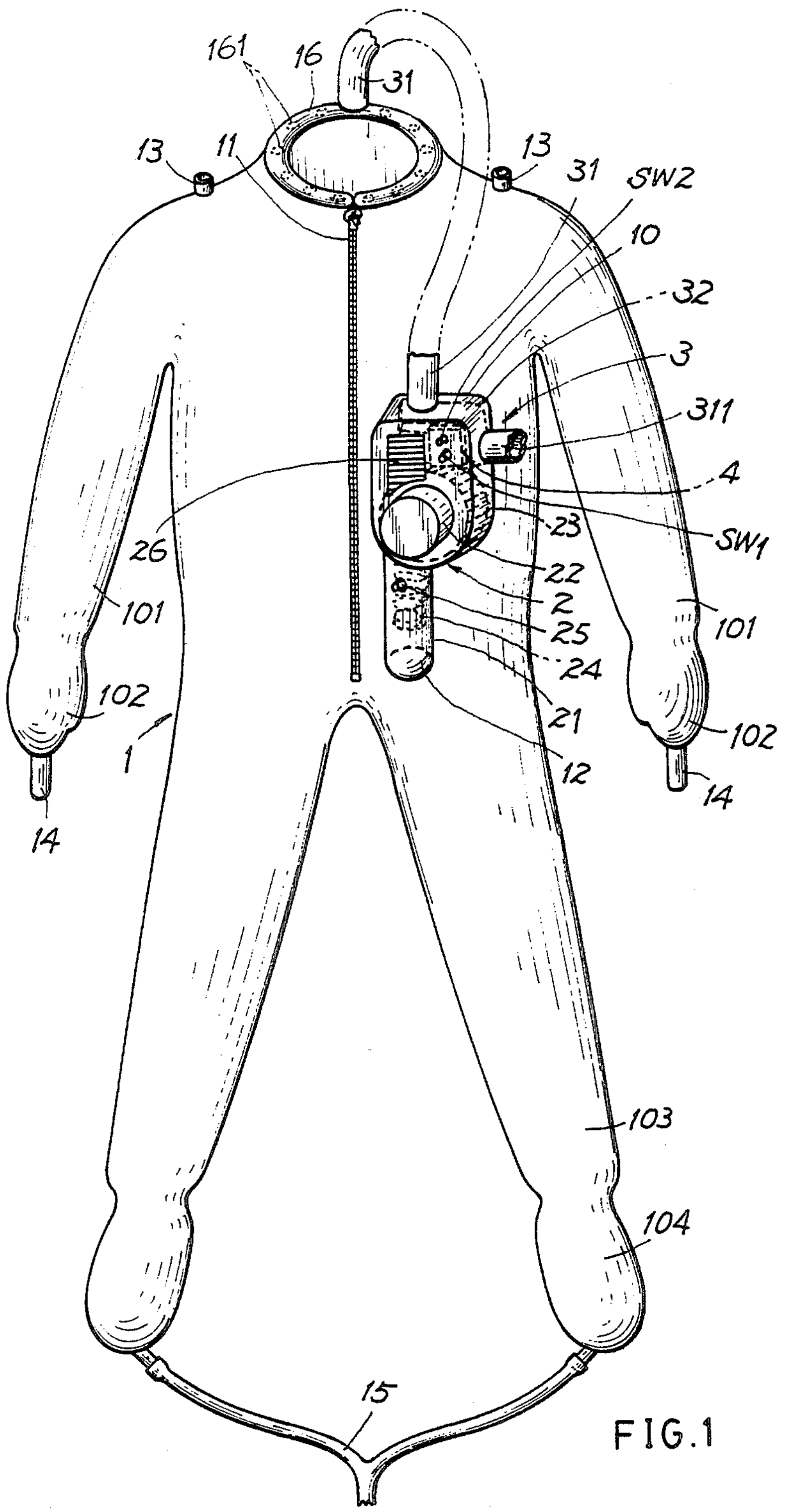
FIG. 1 is an illustration showing the present invention.
Figure 2:
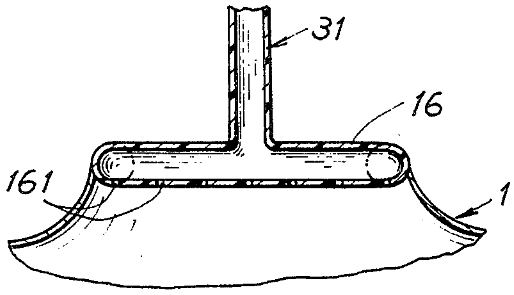
FIG. 2 shows a collar portion of the present invention.

As shown in the figures, the present invention comprises: an one-piece jacket 1, a hot-air supplier 2, a cooling-water supplier 3, and a sequential timing device 4.

The one-piece jacket 1 as made of water-proof and heat-insulating materials includes: a slide fastener 11 longitudinally formed on the central portion of the jacket 1 for a bather's wearing use, a hot-air inlet port 12 formed on a waist portion of the jacket, two upper air vents 13 formed on the shoulder portions of the jacket, two middle air/water discharge tubes 14 respectively formed on two gloves 102 secured with the two sleeves 101, two lower air/water discharge tubes 15 respectively formed on two shoes 104 secured to two trouser hoses 103, and an annular hose 16 formed on the collar portion of the jacket having plural spray holes 161 formed through the hose 16.

The hot-air supplier 2 includes: an air inlet pipe 21 connected with the hot-air port 12 formed on jacket 1, an air fan 23 driven by a motor 22 mounted on a casing 10 formed on a chest portion of the jacket 1, a heating coil 24 inserted in the pipe 21 beyond the fan 23, a temperature controller 25 adjustably controlling the temperature of the coil 24 and the hot-air, and an air suction louver 26 formed on the casing 10 for directing air into pipe 21 for heating purpose.

The cooling-water supplier 3 includes: a water inlet pipe 311 connected with a cooling water source, a solenoid valve 32 formed in the casing 10 and connected with the inlet pipe 311, a water outlet pipe 31 connected between the solenoid valve 32 and the annular hose 16 formed on a collar portion of the jacket 1.

When using the present invention for a bathing, the hot-air supplier 2 is first started by driving the fan 23 and heating the coil 24 so as to deliver a hot air stream through the pipe 21, port 12 into the central portion of jacket 1 and the hot air stream will then be diffused and distributed everywhere within the jacket to warm a bather. Finally, the "waste" air will be discharged through the upper vents 13, middle tubes 14 and lower tubes 15.

Then, the hot-air supplier 2 is switched off and the cooling-water supplier 3 is actuated by opening the solenoid valve 32 to deliver the water stream from pipe 311, and through valve 32, pipe 31 and the hose 16, whereby the cooling water will be sprayed downwardly through the plural spray holes 161 to cool down the bather's body and the "waste" water will be drained through tubes 14 and 15.

Figure 3:
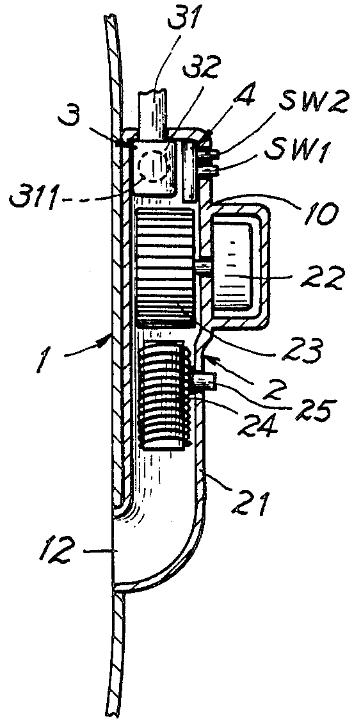
FIG. 3 is a partial sectional drawing showing a hot-air and cooling-water supplier of the present invention.
Figure 4:
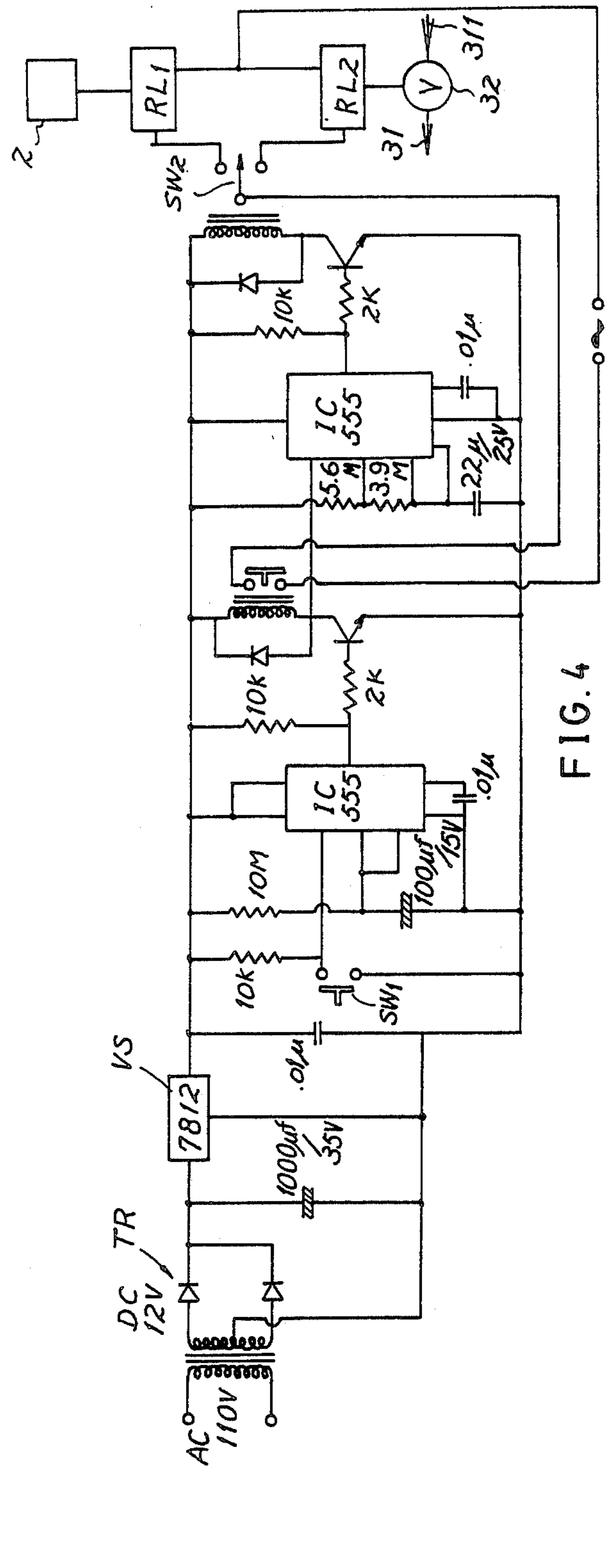
FIG. 4 is an electronic circuit diagram of a sequential timing device of the present invention.
Figure 5:
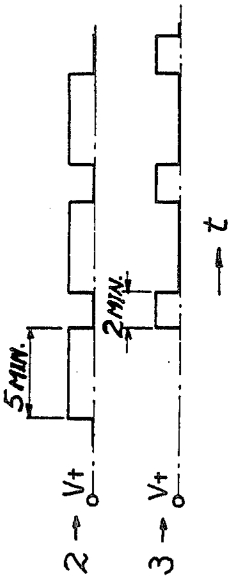
FIG. 5 shows a time sequence operated by the present invention.

For performing the alternative operations of the hot-air supplier 2 and the cooling-water supplier 3, a sequential timing device 4 is provided in this invention as shown in FIGS. 4, 3 and 1, which includes a power transformer and rectifier TR for transforming and rectifying an alternative current for safe use in this invention, a voltage stabilizer VS such as IC 7812 for stabilizing the input voltage, a pair of timing integrated circuits (IC), such as IC 555 for sequentially timing the alternative operation of the hot-air supplier 2 and cooling-water supplier 3, a first relay RL1 adapted for driving the hot-air supplier 2 as actuated by the timing IC, and a second relay RL2 adapted for driving the cooling-water supplier 3 as actuated by the timing IC. The main switch SW1 can be switched on for starting the operation of the timing device 4 as mounted in the casing 1. A second switch SW2 may also be protruded outwardly from the casing 10, adapted for manually switching either hot-air supplier 2 or cooling-water supplier 3. The timing sequence may be so designed to have a hot-air operation period of first five minutes and then a cooling-water operation period of subsequent two minutes, which are then alternatively circulatively repeated, such as, for three cycles [$(5+2)\times 3=21$ minutes], as shown in FIG. 5.

Such a timing sequence can be selected from any conventional electronic devices or any other timing switches. Even, the present invention can be operated manually.

What is claimed is:

1. A portable sauna-bath jacket comprising:

an one-piece jacket having two upper vents formed on its shoulder portions, two middle discharge tubes respectively formed on two gloves secured to two sleeves of the jacket, two lower discharge tubes respectively formed on two shoes secured to two trouser hoses of said jacket, and an annular hose with plural spray holes on said hose formed on a collar portion of said jacket;

a hot-air supplier including an air inlet pipe communicated with an air inlet port formed on a central portion of said jacket, an air fan driven by a motor mounted in a casing formed on a chest portion of said jacket, a temperature-controlled heating coil mounted in the inlet pipe for heating an air stream as driven by the fan and a suction louver formed on the casing for sucking air therein; and a cooling-water supplier including a water inlet pipe connected with a cooling water source, a solenoid valve connected with the water inlet pipe and mounted in said casing, and a water inlet pipe connected between said solenoid valve and said annular hose, whereby upon the switching-on operation of said hot-air supplier, a hot-air stream is delivered into said inlet port and distributed everywhere within said jacket for warming a bather and finally discharged through the upper vents, middle and lower discharge tubes; and upon the alternative switching of said solenoid valve of said cooling-water supplier by switching off said hot-air supplier, a water stream is delivered through the water pipes and said annular hose to spray cooling water through said spray holes for cooling the bather.

2. A portable sauna-bath jacket according to claim 1, wherein said jacket further includes a sequential timing device having a transformer/rectifier transforming and rectifying an alternative current for safe bathing use, a voltage stabilizer stabilizing the input power, and a pair of timing integrated circuits adapted for sequentially actuating a first relay for driving said hot-air supplier and then actuating a second relay for driving said cooling-water supplier alternatively.

* * * * *